United States Patent [19]
Paslin

[11] Patent Number: 5,885,822
[45] Date of Patent: Mar. 23, 1999

[54] METHOD AND SYSTEM FOR GROWING MOLLUSCUM CONTAGIOSUM IN XENOGRAFTS TO IMMUNOCOMPROMISED HOSTS

[75] Inventor: David A. Paslin, 1684 Lexington Ave., San Mateo, Calif. 94402

[73] Assignee: David A. Paslin, San Mateo, Calif.

[21] Appl. No.: 699,744

[22] Filed: Aug. 20, 1996

[51] Int. Cl.$^6$ .............................. C12N 7/00; C12N 7/02; A61K 39/275; A61K 39/12

[52] U.S. Cl. ...................... 435/235.1; 435/239; 424/93.1; 424/204.1; 424/232.1

[58] Field of Search .................................. 435/1.1, 235.1, 435/239; 424/93.1, 204.1, 232.1

[56] References Cited

PUBLICATIONS

Epstein, *Seminars in Dermatology*, vol. 3 184–189 (1992).

Brune, et al., *The Society for Investigative Dermatology, Inc.*, pp. 277–281 (1995).

Buller, et al., "Replication of Molluscum Contagiosum Virus", Virology, vol. 213, pp. 555–669 (1995).

W. Bonnez, et al., "Growth of Molluscum Contagiosum (MC) Virus (V) in a Human Foreskin Xenograft–Severe Combined Immunodeficiency (SCID) Mouse Model", University of Rochester Sch. of Med. and Dent., Rochester, NY 14642 (Abstract).

McFaddeen G, Pace W, Purres J, Dales S; Biogenesis of Poxviruses:Transitory expression of M.contagiosum early functions; Virol. 94 297–313 1979.

Kreider J,Howlett M,Lill N, Barlett G, Zainoo R, Sedlacek T, Mortel R In vivo transformation of human skin with human papillomavirus type 11 from condylomata acuminata; J. Virol. 59(2). 1986.

Sterling J,Stanley M, Gatward G,Minson T Production of human papilloma type16 virions in a keratinocyte cell line J. Virol. 64(12) 6305–6307. 1990.

Bonnez W,Rose R,Da Rin C,Borkuis C,DeMesy Jensen K,Reichman R Propagation of human papillomavirus type 11 in human xenografts using the severe combined immunodeficiency (SCID) mouse and comparison to the nude mouse model Virol 197 455–458. 1993.

DiLoreto D,Epstein L,Lazar E,Britt W,Del Cerro M, Methods in laboratory investigation Cytomegalovirus infection of human retinal tissue:An in vivo model Lab. Invest. 71(1) 141–148. 1994.

Postlethwaite R., Molluscum Conagiosum: A Review, Arch. Environ. Health 1979, 21:432–452.

*Primary Examiner*—Laurie Scheiner
*Assistant Examiner*—Jeffrey S. Parkin
*Attorney, Agent, or Firm*—Wilson Sonsini Goodrich & Rosati

[57] ABSTRACT

A method and system is provided for the growth of the molluscum contagiosum virus in human skin xenografted to an immunocompromised host. A human skin graft is infected with molluscum contagiosum virus attached to or beneath a skin section of the immunocompromised host. According to the method, a section of skin of an immunocompromised host is prepared for receiving a human skin xenograft which is then placed onto or into the host. The human skin is infected with the molluscum contagiosum virus. The animals are monitored and the newly grown virus and its products are harvested for further study.

23 Claims, 11 Drawing Sheets

METHOD AND SYSTEM FOR GROWING MOLLUSCUM CONTAGIOSUM IN XENOGRAFTS TO IMMUNOCOMPROMISED HOSTS

BACKGROUND OF THE INVENTION

1. Field of the Invention

The present invention relates to a system and method for growing molluscum contagiosum virus (MCV) in human keratinocytes and, more specifically, for growing MCV in human keratinocytes through a xenograft to an immunocompromised host.

2. Description of Related Art

Molluscum contagiosum virus (MCV) causes an asymptomatic, indolent, harmless infection of human skin. However, in people with impaired immunity, especially in people with acquired immune deficiency syndrome (AIDS), MCV often becomes morbid with the development of many nodules some of which are large in size.

MCV is a member of the parapoxvirus family, along with orf virus, pseudocowpox (milker's nodule) virus, yaba virus and tanapox virus. MCV can be identified in skin biopsy samples by the presence of large intracytoplasmic inclusion bodies within infected keratinocytes. MCV lacks known close viral relatives and is serologically distinct from any other characterized pox virus. Fields BN and Knipe DM (eds.) Fields Virology 2nd Ed. Raven Press, New York. 1990, p. 31. Purified virions of MCV resemble those of vaccinia, a member of the orthopox virus group, in morphology, physical properties and chemical composition. Fields BN and Knipe DM (eds.) Fields Virology 2nd Ed. Raven Press, New York. 1990, p. 2130. However, although the vaccinia virus has been readily grown in culture, successful growth of MCV in culture has been elusive.

The difficulty associated with growing MCV in culture appears to be due to a defect in the expression of the genome in MCV. Mouse embryo cells infected with vaccinia have been shown to synthesize viral RNA and polypeptides. The same cells infected with MCV do not synthesize viral RNA and viral polypeptides. Shand, et al., *J. Gen. Virol.* (1976) 33:281–295. In culture, MCV has been shown to induce a nontransmissible cytopathic effect, but does not produce infectious progeny. Francis, et al., *J. Virology* (1976) 19:382–388. With the exception of one report (Buller, et al., *Virology* (1995) 213:655–659), attempts to grow MCV off a human host have repeatedly failed. For example, MCV was found not to grow on the chorioallantoic membrane of chick embryos, on normal human skin grafted onto the chorioallantoic membrane or in cultures of human fetal skin. Postlethwaite, *Arch Environ Health* (1970) 21:432–452. MCV has been found not to grow following inoculation into the skin, footpad, peritoneal cavity or brain of hairless mice. MCV has also been found not to grow in cultures of human embryonic liver or lung or in cultures of African green and cynomolgus monkey kidney cells or in cultures of human amnion and human foreskin. Postlethwaite, *Arch Environ Health* (1970) 21:432–452.

Failed attempts to grow MCV in the skin or other tissues of mice, guinea pigs, rabbits, sheep, apes and chimpanzees have also been reported. Warren J: Infections of minor importance: Molluscum contagiosum. In Rivers T M, Horsfall Jr F L: Viral and Rickettsial Infections of Man, 3rd Ed. Pitman Medical Publishing Co Ltd, London, 1959, pp. 908–909. Failed efforts to grow MCV in tissue culture from explants of diseased skin from patients with molluscum contagiosum and in organ cultures of healthy adult human skin inoculated with extracts of MCV papules have also been reported. Prose, et al., *Am. J. Path.* (1969) 55:349–366.

In view of the difficulties associated with growing MCV in host cells, a need currently exists for a method and host system for growing MCV. A further need exists for a system and method for growing MCV in human cells.

SUMMARY OF THE INVENTION

A system and method is provided for expressing molluscum contagiosum virus (MCV) in human keratinocytes using an immunocompromised host. The method for growing molluscum contagiosum virus (MCV) in human keratinocytes includes exposing a capillary bed surface immunocompromised host, attaching a piece of human skin to the host such that a dermal side of the human skin is in contact with the exposed capillary bed surface, and infecting the human skin with MCV. Infection of the human skin with MCV can be performed before, during or after grafting of the human skin to the host.

According to the method, the step of exposing a capillary bed surface may include removing a section of skin from a body of the immunocompromised host. Alternatively, the step of exposing a capillary bed surface may include uplifting a section of skin from a body of the immunocompromised host so as to expose the capillary bed without completely disconnecting the skin section from the host body. According to this embodiment, the step of attaching the piece of human skin may include attaching the human skin to either the body of the immunocompromised host or the uplifted section of host skin and reattaching the uplifted host skin section to the body of the immunocompromised host. In one embodiment, the step of uplifting the host skin section is performed such that the exposed capillary bed surface is positioned on the host body. In another embodiment, the step of uplifting the host skin section is performed such that the exposed capillary bed surface is positioned on the uplifted host skin section.

A system is also provided for sustained expression of molluscum contagiosum virus which includes an immunocompromised host having a capillary bed surface and a human skin sample infected with MCV in contact with the capillary bed surface of the immunocompromised host. In one embodiment, a host skin section is removed to expose the capillary bed surface and the human skin sample is attached to the capillary bed surface at the location where the host skin section is removed. In another embodiment, a section of skin of the immunocompromised host is uplifted from a body of the immunocompromised host to expose the capillary bed surface and the human skin is attached to either the body of the immunocompromised host or the uplifted section of host skin and the uplifted section of host skin is reattached to the body of the immunocompromised host. In one variation of this embodiment, the exposed capillary bed surface is positioned on the host body. In another variation, the exposed capillary bed surface is positioned on the uplifted host skin section.

BRIEF DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION

The present invention relates to a system and method for achieving growth of molluscum contagiosum virus (MCV) in human keratinocytes in which a xenograft of human skin is placed on or within an immunocompromised host and in which MCV growth in the human keratinocytes is achieved. According to the present invention, MCV growth in the grafted skin is preferably sustained for at least two weeks, more preferably at least four weeks. As discussed herein, sustained growth of MCV has been achieved for significantly longer periods of time than four weeks.

Figure 1:
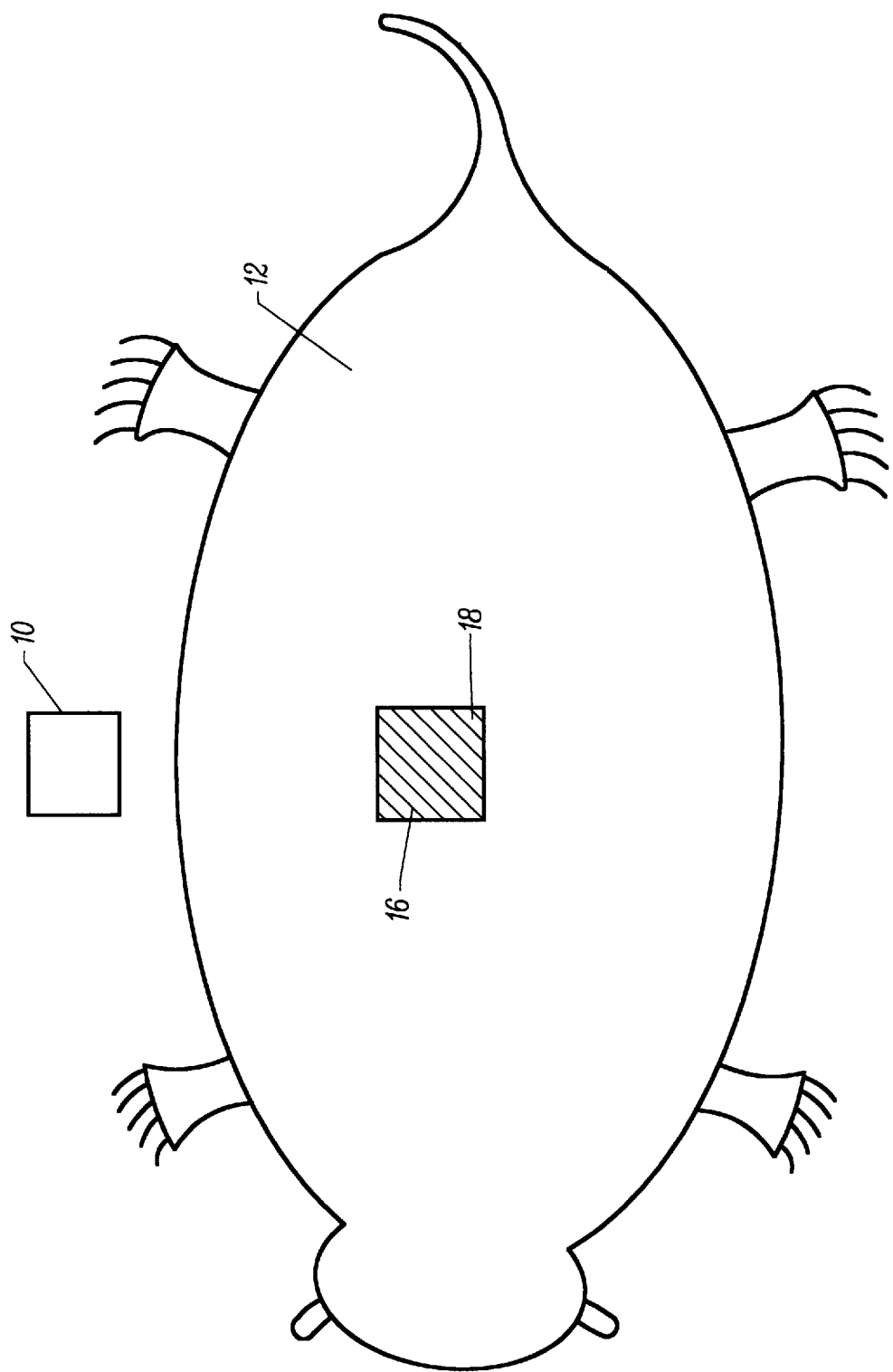
FIG. 1 is a drawing that illustrates a step in the method in which an area of skin of an immunocompromised host is prepared to receive a piece of human skin, placed exteriorly.
Figure 2:
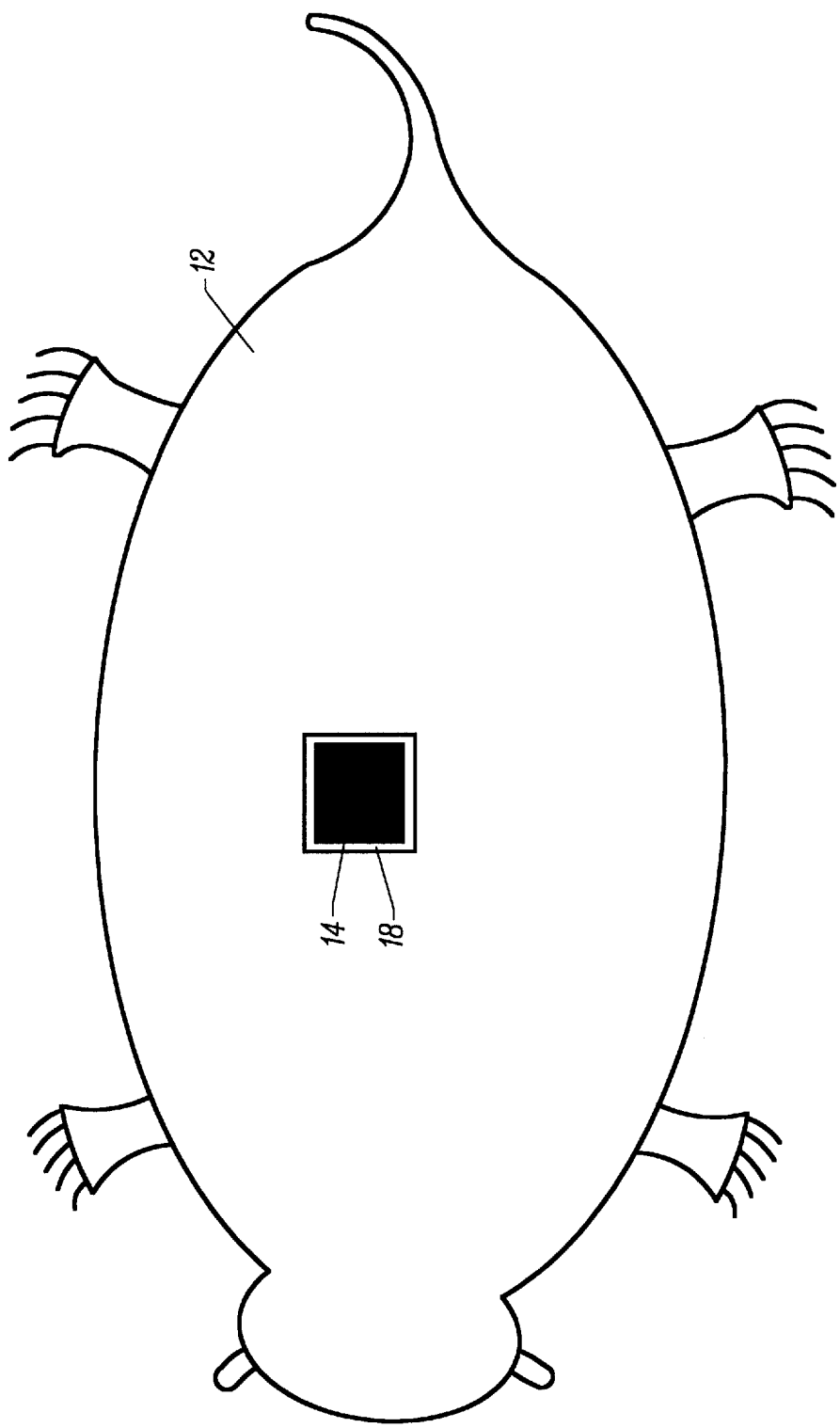
FIG. 2 is a drawing that illustrates placement of the human skin onto the prepared area of the host.

Methods for growing MCV according to the present invention will now be described and are illustrated in FIGS. 1–6. FIGS. 1–2 illustrate a method for growing MCV in an external skin graft. As illustrated in FIG. 1, an area 10 of the host's skin 12, in this instance a mouse, is removed. The area 10 should be approximately the size of the piece of human skin 14 to be grafted. The host skin area 12 that is removed is dissected from the host in such manner as to leave the fascial capillary bed 16 attached to the underlying panniculus carnosus 18. As illustrated in FIG. 2, a human skin graft 14 is then placed over the intact capillary bed 16 and attached to the immunocompromised host at the wound edges, preferably with nylon sutures and permabond glue between the sutures.

Figure 3:
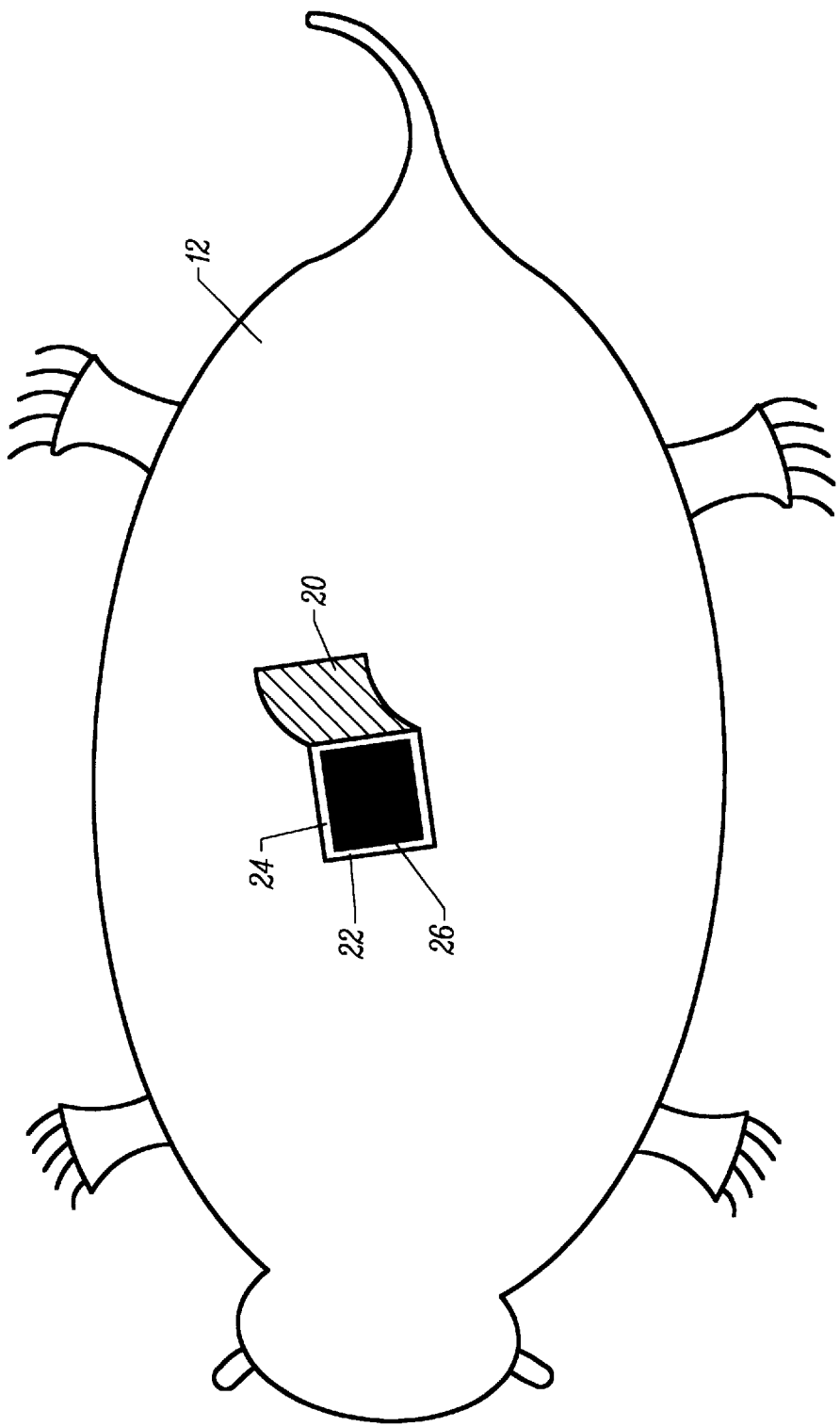
FIG. 3 is a drawing that illustrates a step in the method of preparing a buried graft wherein the capillary bed is attached to the panniculus carnosus on the host body and the human skin is attached to the host body such that the epidermal side of the human skin is facing up away from the body of the host.
Figure 4:
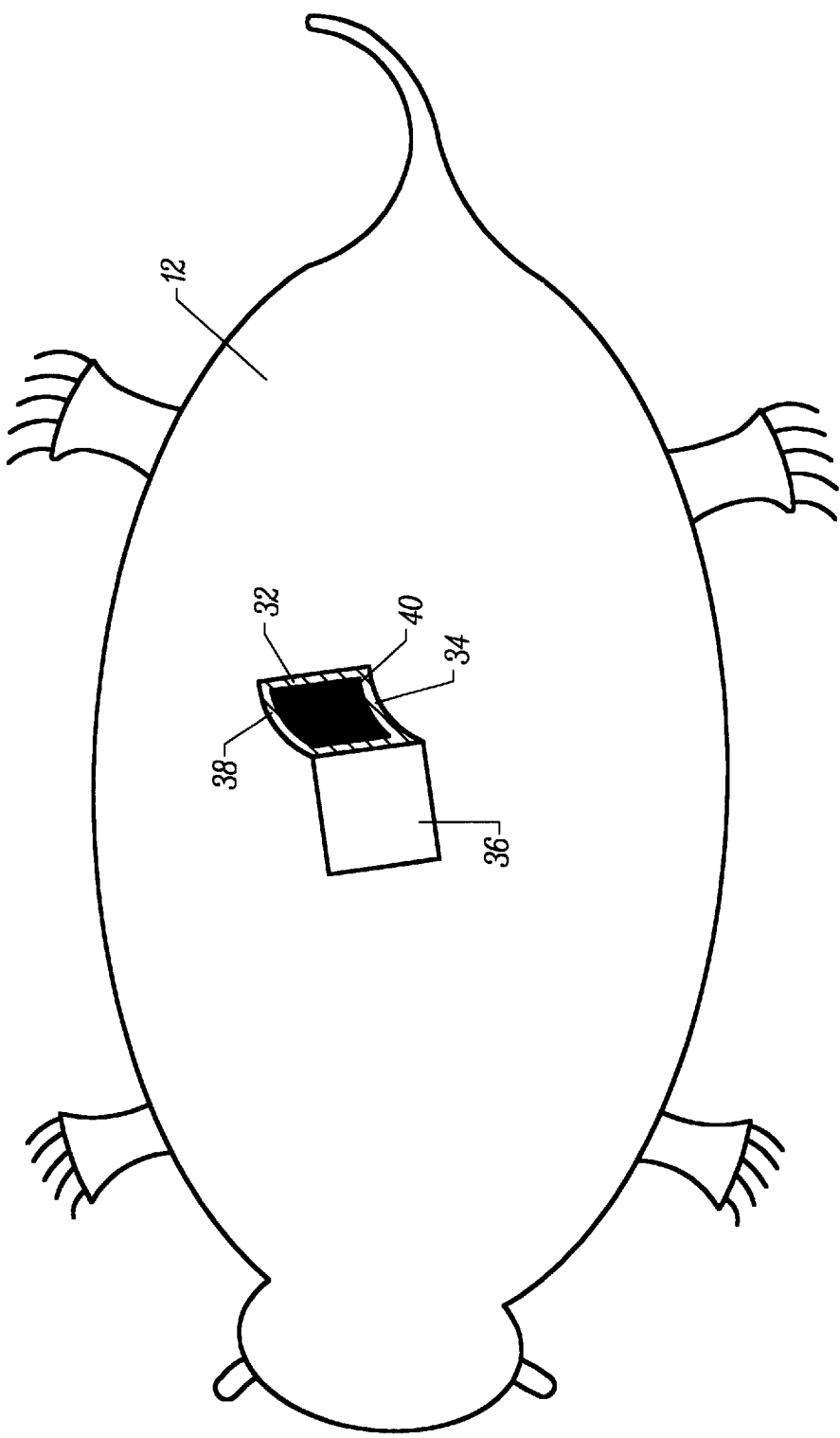
FIG. 4 is a drawing that illustrates a step in the method of preparing a buried graft wherein the capillary bed is retained with the uplifted section and the human skin is attached to the uplifted section of host skin such that the epidermal side of the human skin is facing down toward the body of the host when the uplifted section is reattached to the capillary bed of the host.
Figure 5:
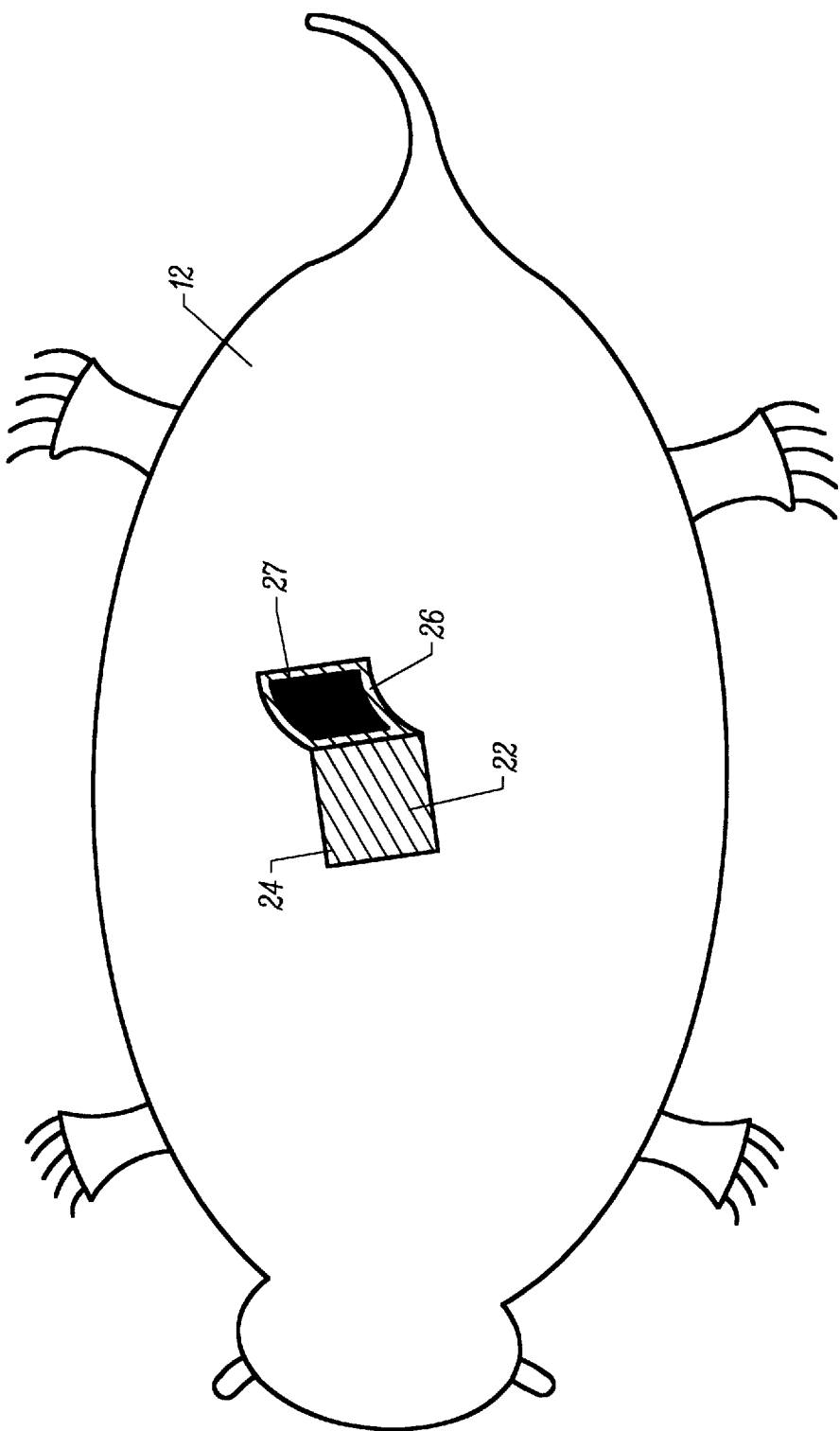
FIG. 5 is a drawing that illustrates a step in the method of preparing a buried graft wherein the capillary bed is attached to the panniculus carnosus on the host body and the human skin is attached to the uplifted section of host skin such that the epidermal side of the human skin is facing up away from the body of the host when the uplifted section is reattached to the capillary bed of the host.
Figure 6:
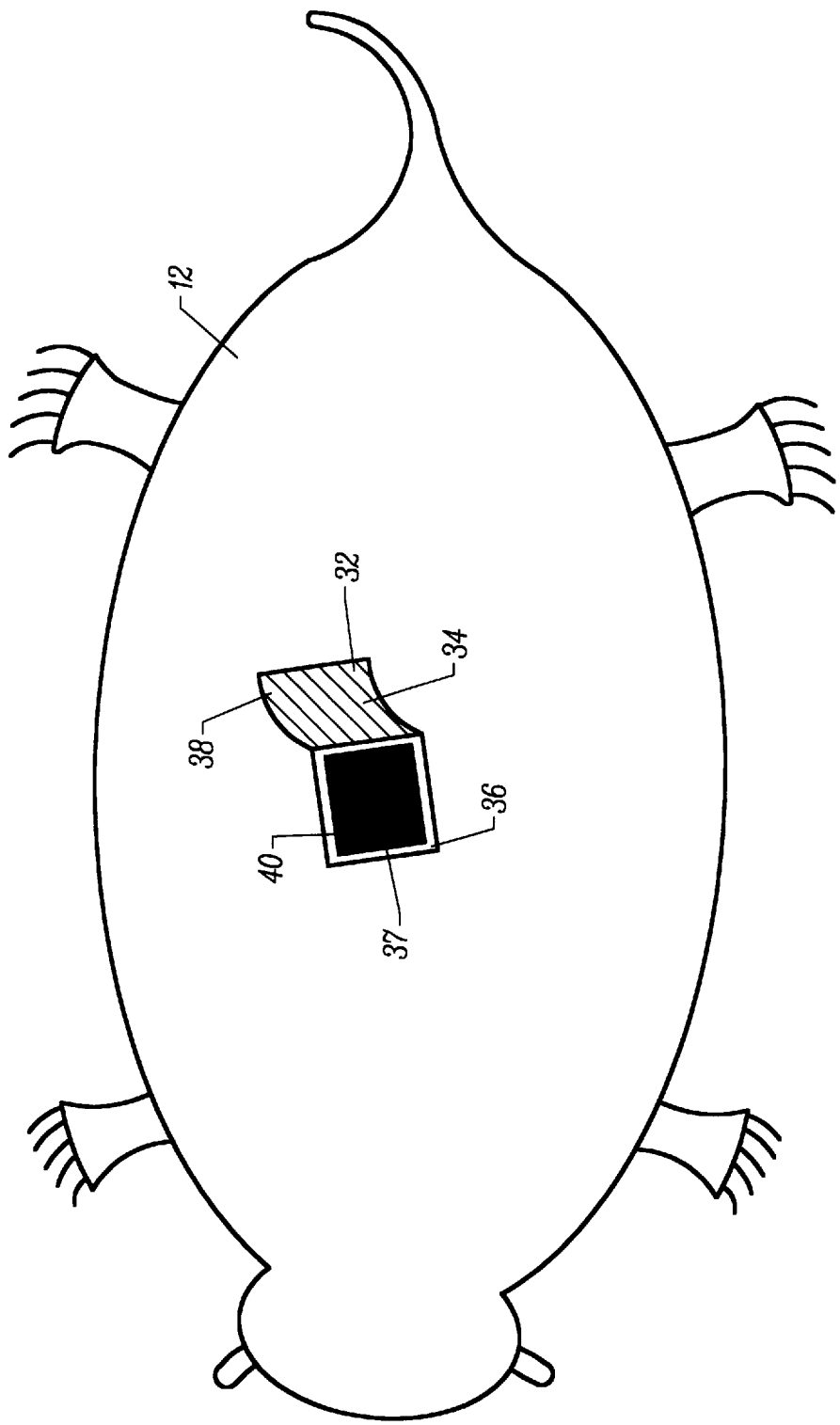
FIG. 6 is a drawing that illustrates a step in the method of preparing a buried graft wherein the capillary bed is retained with the uplifted section and the human skin is attached to the host body such that the epidermal side of the human skin is facing down toward the body of the host.

FIGS. 3–6 illustrate methods for growing MCV in a buried skin graft. FIGS. 3 and 5 illustrate methods for growing MCV wherein the capillary bed is attached to the panniculus carnosus on the host body. In the embodiments illustrated by these figures, the epidermis of the grafted skin is facing down toward the capillary bed on the body of the host. FIGS. 4 and 6 illustrate methods for growing MCV wherein the capillary bed is attached to an uplifted section of skin on the host. In the embodiments illustrated by these figures, the epidermis of the grafted skin is facing up away from the body of the host and toward the capillary bed on the uplifted section of skin. The embodiments illustrated by FIGS. 3 and 4 are preferred because the grafted skin is directly attached to the capillary bed.

As illustrated in FIGS. 3 and 5, a piece of host skin 20 is carefully incised and uplifted on 3 sides, although a straight line incision and careful dissection is also satisfactory. The incision is made in such a manner as to leave behind an intact fascial capillary bed 22 on the panniculus carnosus 24.

As illustrated in FIG. 3, a piece of human skin 26, generally of a slightly smaller size than the exposed capillary bed 22 (size may vary) is sewn to the panniculus carnosus 24, the dermal side (not shown) of the human skin facing down toward the host body such that it is in contact with the capillary bed 22. Alternatively, as illustrated in FIG. 5, the piece of human skin 26, may be sewn to the underside of the incised host skin 20 such that the dermal side 27 of the human skin faces down toward the host body when the incised host skin 20 is resown over the capillary bed. After attachment of the human skin, the incised host skin 20 is resown over the capillary bed.

FIGS. 4 and 6 illustrate a method for growing MCV in a buried skin graft where the epidermis of the graft is facing up away from the body of the host. As illustrated in FIGS. 4 and 6, a section 32 the host skin is uplifted as in FIGS. 3 and 5, but the dissection is performed such that the intact fascial capillary bed 34 is freed from the panniculus carnosus 36 to allow the capillary bed 34 to remain attached to the undersurface 38 of the uplifted section 32 of the host epidermis.

As illustrated in FIG. 4, a piece of human skin 40, generally of a slightly smaller size than the exposed capillary bed 22 (size may vary), may be sewn to the underside of the incised host skin 32 such that the dermal side 37 of the human skin 40 is in contact with the capillary bed 22. After attachment of the human skin, the incised host skin 32 is resown over the capillary bed. When the incised host skin 32 is resown, the human skin faces away from the host body.

Alternatively, as illustrated FIG. 4, the piece of human skin 40 may be sewn to the panniculus carnosus 24 such that the dermal side 42 of the human skin 40 faces away from the host body. As a result, the dermal side 37 of the human skin 40 is in contact with the capillary bed 22 when the incised host skin 32 is resown over the capillary bed.

According to the present invention, the skin graft may be from a postnatal human of any age. For example, the skin may be from infantile, childhood adolescent, adult or senescent skin. Types of human skin grafts that may be used include, but are not limited to, foreskins, glabrous skins, mucous membranes and hair bearing skins.

Types of immunocompromised hosts which may be used in the present invention include genetically immunodeficient mammals such as is found among strains of mice and rats. Specific examples of genetically determined immunocompromised hosts which may be used include SCID mice, NOD SCID mice, nude mice, N III nude mice and the variants of nude rats.

The system and method of the present invention may also use as an immunocompromised host an immune privileged site, such as a hamster cheek pouch and the aqueous chamber of a rabbit eye, further enabled by exogenous immune suppression via drugs such as corticosteroids, Cyclosporin, FK 506, Rapamycin, 15-Deoxyspergualin, Mycophenolate Mofetil and Brequinar Sodium or via irradiation or via thymectomy.

The xenograft may be positioned in place of a piece of immunocompromised host skin (referred to herein as an external graft) or beneath the immunocompromised host skin (referred to herein as a buried graft). Involution and shrinkage of xenograft have been regularly observed when grafts are positioned on the surface of the host in place of a piece of the immunocompromised host skin. Accordingly, in a preferred embodiment, the xenograft is positioned beneath the surface of the host skin as a buried graft.

As illustrated in FIGS. 3–6, buried skin xenografts may be positioned such that the graft is positioned with the epidermal side facing down toward the body of the host (FIGS. 3–4) or up away from the body of the host (FIGS. 5–6). Grafts buried with the epidermal side up have been frequently observed to become externalized. When externalized, these grafts usually shrank, whereas those grafts buried with the epidermal side down tend to gradually roll into cysts and endure. However, the yield of MCV does not appear to be significantly different between grafts buried epidermal side up or down. Accordingly, in a preferred embodiment, the xenograft is positioned beneath the surface of the host skin with the epidermal side either up or down.

Infection of the human skin to be grafted with MCV may be performed before, during or after the skin is grafted to the immunocompromised host. A variety of methods may be used to infect the human skin sample. For example, the skin sample may be infected with MCV by grinding a suspension of MCV into the skin. Alternatively, a suspension of MCV may be injected into the skin. MCV may also be introduced topically, optionally with the assistance of such agents as creams, ointments, gels, detergents, enzymes, biologics, liposomes, by dermajet and by ultrasound.

Figure 7:
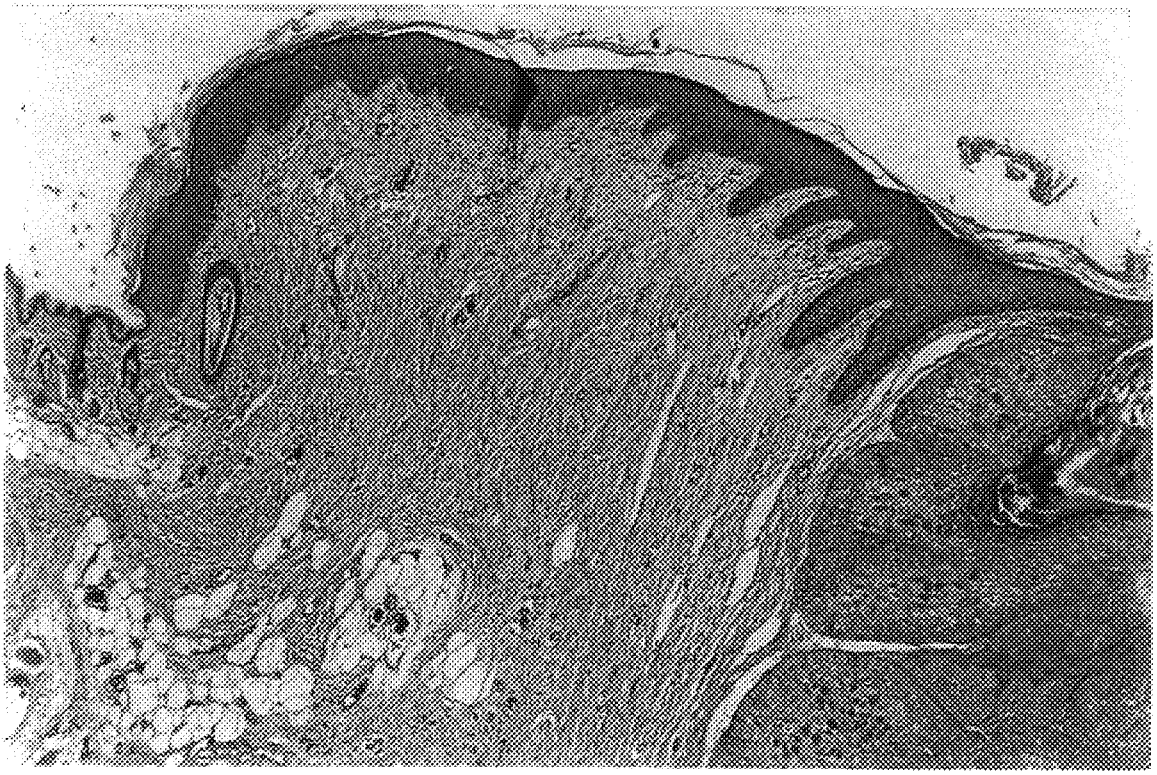
FIG. 7 is a photomicrograph that illustrates: on the left, the epidermis of a NOD/SCID mouse; in the center, a human foreskin xenografted to that mouse; on the right, growth of MCV in that human foreskin.
Figure 8:
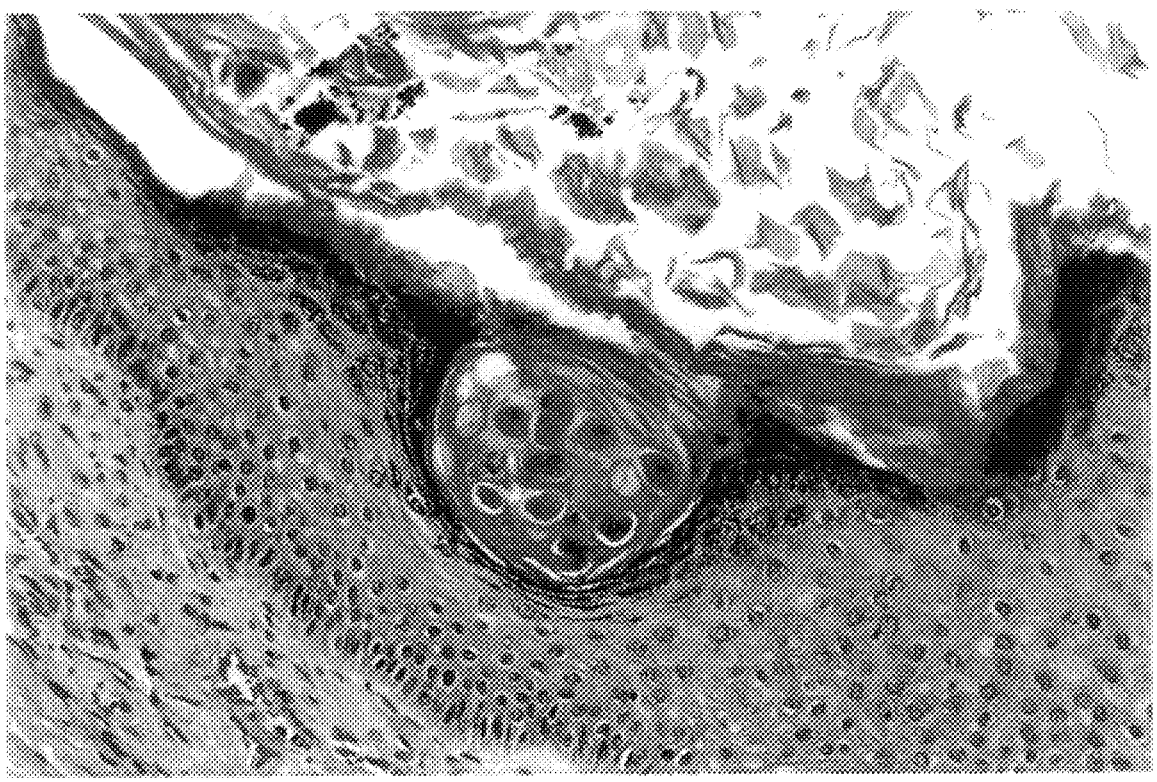
FIG. 8 is a photomicrograph that illustrates growth of MCV on the inner surface of a cyst from a human foreskin that had been buried beneath the skin of a NOD/SCID mouse with the epidermal side facing down toward the body of the mouse.
Figure 9:
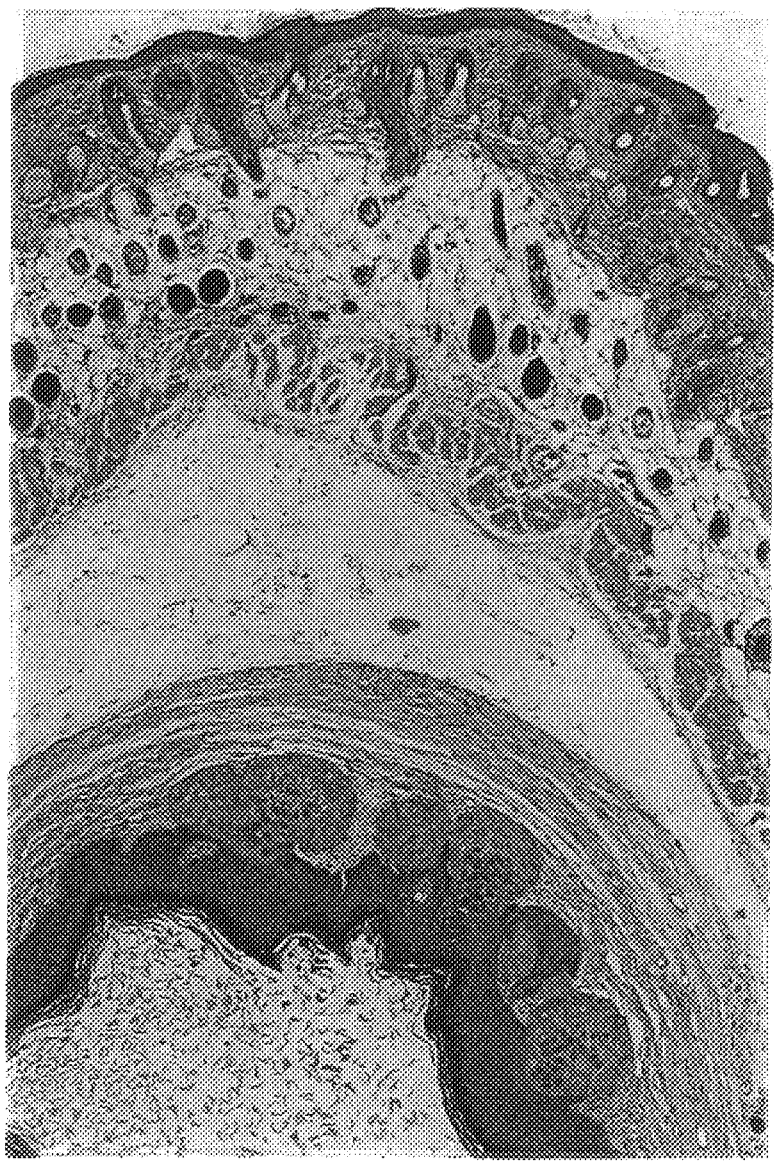
FIG. 9 is a photomicrograph that illustrates growth of MCV on the outer surface of a cyst from a human foreskin that had been buried beneath the skin of a N III nude mouse with the epidermal side facing down toward the body of the mouse.
Figure 10:
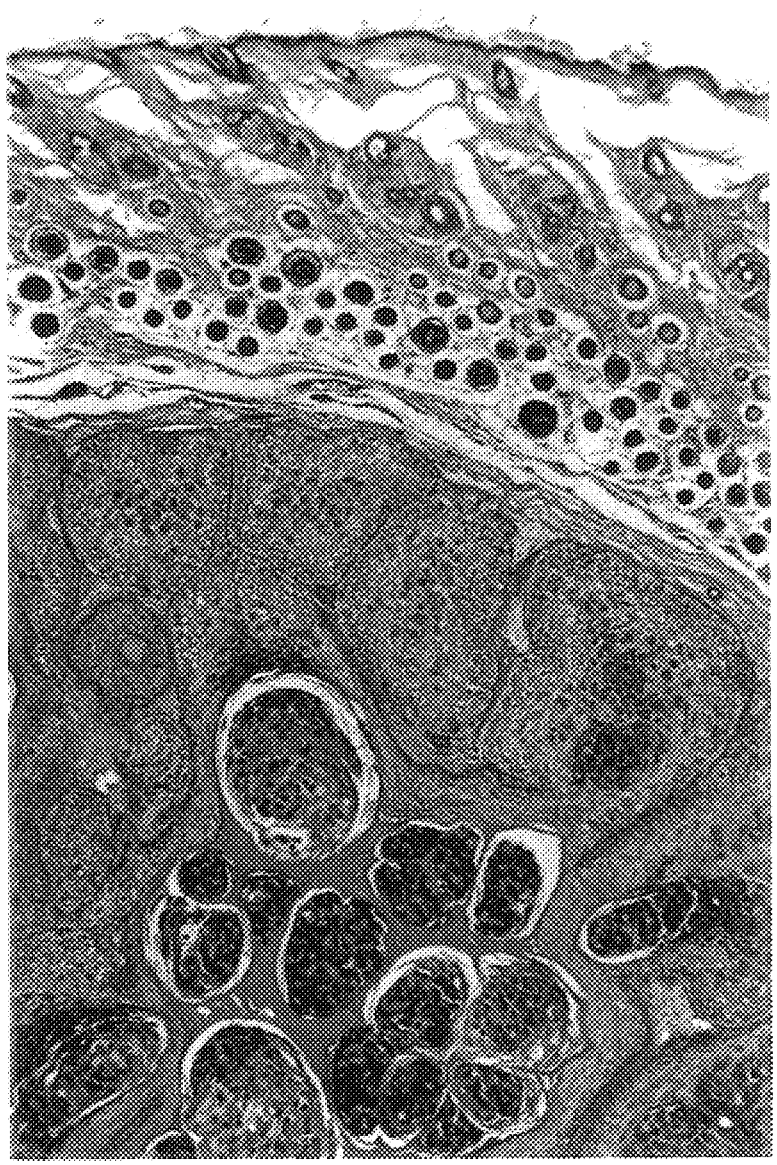
FIG. 10 is a photomicrograph that illustrates the massive growth of MCV that may occur (on and) beneath the skin of a SCID mouse—in this instance in human adult skin that had been placed externally onto the skin of the mouse.
Figure 11:
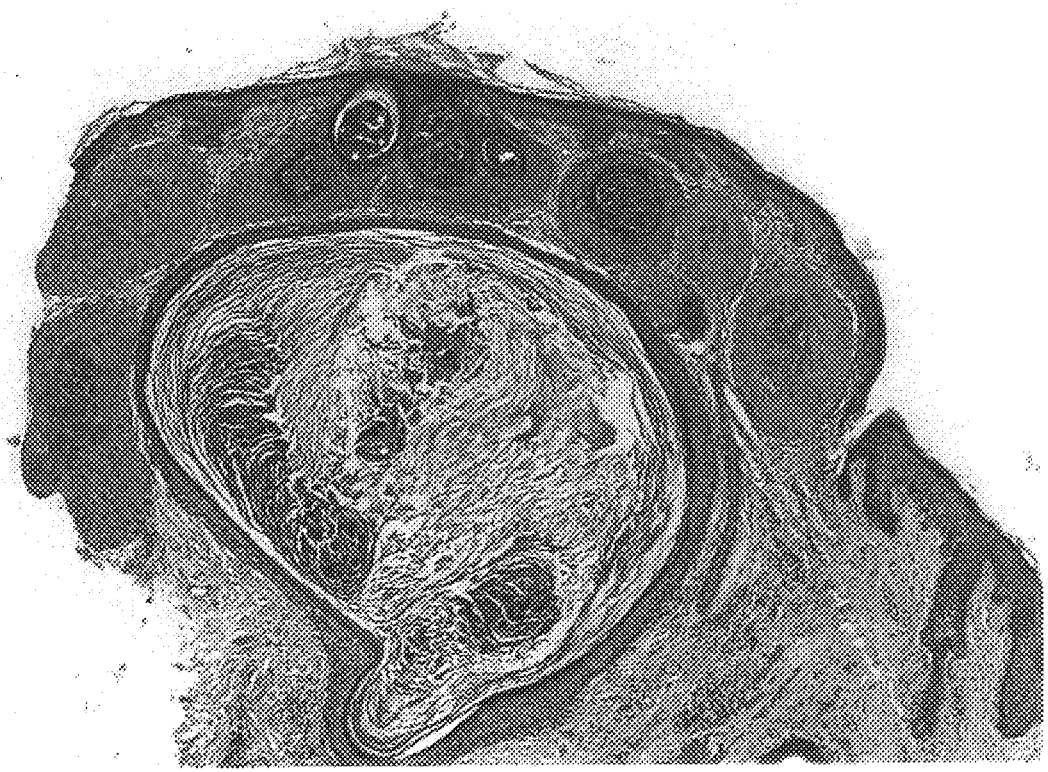
FIG. 11 is a photomicrograph that illustrates growth of MCV within a cyst in a natural infection of a patient.

FIG. 7 provides a photomicrograph showing growth of MCV in a human foreskin grafted to a NOD/SCID mouse according to the embodiments described above. On the left side of the photomicrograph, FIG. 7 shows murine skin; on the center, it shows human foreskin engrafted to the murine skin; on the right side, it shows MCV growing within the epidermis of the foreskin. FIG. 8 is a photomicrograph that shows the growth of MCV on the inner surface of a human foreskin cyst buried beneath the skin of a NOD/SCID mouse. FIG. 9 is a photomicrograph that shows the growth of MCV on the outer surface of a human foreskin cyst buried beneath the skin of a N III nude mouse. FIG. 10 is a photomicrograph that shows MCV growth in (and on) an adult human skin grafted to the surface of a SCID mouse. As can be seen from this figure, massive MCV growth can be obtained according to the present invention. FIG. 11 is a photomicrograph that shows the unaided growth of MCV within a cyst in a natural infection of a patient.

Without being bound by theory, it would appear that growth of MCV in human keratinocytes requires mammalian blood or tissue factors which may be provided by murine or other mammalian hosts. It seems highly likely that postnatal human keratinocytes are required to support growth of MCV. For example, MCV has been found to grow on or in human foreskins and adult skins obtained from postnatal subjects, although not on or in fetal skins. These findings are consistent with Postlethwaite's observation that no growth of MCV occurred following inoculation of MCV into organ cultures of human fetal skin. Postlethwaite, *Arch Environ Health* (1970) 21:432–452. In Postlethwaite's study, the organ cultures lasted only 15 days and the fetal skin did not have the nutritional and serous factorial support of a mammalian host. The current experiments indicate that growth of MCV does not occur in human fetal skin grafts even when such grafts are sustained for at least 19 weeks in an immunocompromised mammalian host. This suggests that fetal human skin keratinocytes lack factors of sufficient maturation or differentiation to enable growth of MCV. These factors appear to be present at the time of full term births in view of the growth of MCV in human full term foreskin grafts.

In addition to growing on the surface of the host, it is interesting that MCV growth is observed beneath the host skin surface on the inside of cyst walls, as illustrated in FIG. 8, and on the outside of cyst walls, as illustrated in FIG. 9. Growth of MCV on the outside of cyst walls is strong evidence that growth of MCV in keratinocytes most probably arises in and from basal layer keratinocytes. Growth of MCV on the surface of the mouse and on the outside of cyst walls appears to be aerobic. However, growth of MCV on the inside of cysts suggests that MCV can also grow anaerobically. This is occasionally seen in the natural human host, as illustrated in FIG. 11. Further, growth of MCV at cool surface temperatures may be anticipated based on clinical findings, yet growth at higher subcutaneous temperatures occurs equally well if not more readily, based on frequencies of growth seen in the experiments conducted to date. It might be predicted that MCV could grow in human epidermal keratinocytes through the range of conditions under which such keratinocytes are known to live in the natural human host.

The following describes the procedures for growing MCV in neonatal, adult and other human skins externally and internally engrafted in SCID and nude mice and presents the experimental results observed. Further, objectives and advantages of the present invention other than those set forth above will become apparent from the procedures which are not intended to limit the scope of the present invention.

Growth of MCV in Postnatal Human Skin Xenografted to Immunocompromised Mice

The following procedures describe a method used in the present invention for the growth of MCV in postnatal human skins which have been xenografted onto and beneath the skin of immunosuppressed mice.

a) Molluscum contagiosum virus (MCV)

MCV used in this method was obtained by harvesting MCV papules by curettage from healthy children patients. The presence of MCV in these papules was proven by biopsies which show the pathognomonic intracytoplasmic MCV inclusion bodies within the infected keratinocytes.

Once harvested, the papules were immediately placed in thawed Dulbecco's Modified Eagle Medium, low glucose (MEM) which was obtained from GIBCO Laboratories, Cat. No. 320-1600. Dulbecco, et al. *Virology* 8 396 (1959); Smith, et al. *Virology* 12 185–196 (1960); Tissue Culture Standards Committee, In Vitro 8 93. Dulbecco's MEM, so constituted, is stored as a stock solution at −20° C. The MCV papules were stored in thawed Dulbecco's MEM at 4° C. for between 2 and 20 weeks until they were inoculated onto or into xenografted human skin.

MCV was found to remain viable for at least 20 weeks when kept in Dulbecco's MEM at 4° C. Unlimited storage of MCV may be possible if the virus is kept frozen at −20° C. Further, donor human skin in Dulbecco's MEM at 4° C. retained viability for at least 8 weeks before transplantation. Almost all of the transplantations were done, however, within 4 weeks of harvesting the donor skin, and the majority were done within one week of harvest.

The viability of each sample of stored MCV was examined for cytopathic effect in fetal human diploid lung cells maintained in Eagles's salt solution (GIBCO Laboratories, Cat. No. 310-4230; Eagle, *Science* 130 432 (1959) and Earle's salt solution (GIBCO Laboratories) salt solutions with 10% fetal bovine serum. Cytopathic effect was detected by placing 1–2 papules in 0.3 to 0.4 ml of Dulbecco's MEM in a microfluge vial. The papules were ground with a glass stirring rod, then centrifuged at 12,000 rpm for 10 seconds. The supernatant, containing cell-free viral particles, was pipetted 100 μL onto a monolayer of fetal human diploid lung cells at 37° C. and examined at 48, 72, 96 and 120 hours for cytopathic effect.

b) Mice

Breeding stocks of CB-17-scid/scid and NOD/LtSz-scid/scid mice were generously donated by Dr. Len Schultz (Jackson Laboratories-Bar Harbor, Me.). SCID mice lack mature B and T lymphocytes and the NOD/LtSz-scid/scid strain also lack natural killer (NK) cells. Bosma, et al., *Nature* (1983) 301:527–530; Shultz, et al., *J. Immunol.* (1995) 154:180–191. The athymic 129 J-nu/nu strain was developed at the California Dept of Health Services by backcrossing N:NIH (S)II-nu/nu mice for >10 generations onto 129 J mice obtained from Jackson Laboratories. Azar, et al. *J. Nat'l Cancer Inst.* (1980) 65:421–430. Breeding stock of N III-nu/nu mice were generously provided by Dr. Carl T Hansen of the National Institutes of Health in Besthesda, Md. Andriole, et al. *J. Immunol.* (1985) 135:2911–2913. The 129nu/nu strain lacks B and T lymphocytes. The N III-nu/nu mice lack B, T and NK lymphocytes. Azar, et al. *J. Nat'l Cancer Inst.* (1980) 65:421–430; Andriole, et al. *J. Immunol.* (1985) 135:2911–2913.

c) Human donor skins

Three different types of human donor skins were used in this method, specifically, adult human skins, human foreskins and fetal skins.

The human donor skins were obtained from normal adult human skins which were removed from selected surgical specimens. These surgical specimens were commonly the uninvolved ends of basal cell carcinoma excisions. These triangular or rectangular pieces of skin, approximately 1 to 2 cm in diameter, were placed in thawed Dulbecco's MEM immediately after surgical removal and were stored at 4° C. until use.

Human foreskins were obtained from newborns at hospital circumcisions and were processed in a manner similar to that used for the adult skins.

Fetal skins were obtained from 14 to 24 week old fetuses and were harvested at the time of abortion and processed as described above with regard to adult human skins.

d) Grafting Human Skin to Mice

Human donor skin was grafted to immunocompromised mice by the following procedure. First, the mice were anesthetized by intramuscular injection of 0.10 to 0.15 ml of Ketaset (Ketamine HCl, Aveco-Fort Dodge, Iowa, 3 mg/25 g mouse weight) combined with Rompun (xylazine HCL, Lloyd Laboratories-Shenandoah, Iowa, 0.3 mg/25 g mouse weight). Hair on the backs of CB17-SCID and NOD SCID mice was shaved. Exposed murine skin, approximately the size of the donor human skin to be grafted, was dissected free from underlying fascial blood supply. A human donor piece was then trimmed—mostly of subcutaneous fat in adult skins and mostly of mucinous ground substance in neonatal skins. The trimmed skin was sewn at the corners to the murine skin surrounding the defect using 6-0 nylon (Ethicon) suture and secured with Permabond glue.

Human skins were also sewn onto fascial blood supply buried beneath the surface of the murine skin, orienting the human epidermal surface up or down. The murine skin was then closed by running uninterrupted 6-0 nylon suture reinforced by Permabond glue. Garamycin ointment was applied to each would to reduce the risk of infection, and the wound was then covered by Adaptic gauze secured with Permabond glue.

e) Inoculation of Grafted Skin with MCV

Suspensions of 1–4 MCV papules in 0.1 ml of Dulbecco's MEM, were inoculated into the xenografts either by grinding drops of viral suspension into donor epidermis with a pear shaped diamond fraize or by intradermal injection of up to 0.1 ml per xenograft. Mice were biopsied and/or sacrificed from 19 to 42 weeks after inoculation of the human xenografts with MCV.

f) Viability of MCV Viral Growth in Cell Culture

Viability of MCV stored in Dulbecco's MEM at 4° C. from 4 to 23 weeks was demonstrable from random samples of MCV so stored whether examined at 48, 72, 96 or 120 hours after placement of viral supernatant on a monolayer of fetal human diploid lung cells. Eight such samples were examined and of these, 7 showed cytopathic effect, demonstrating the presence of infectious particles. Of these 7, 5 had large numbers of infectious particles—large being defined as cytopathic effect in at least 50% of the diploid lung cells. MCV stored in Dulbecco's MEM at 4° C. for as long as 23 weeks showed >80% cytopathic effect on this assay.

g) Growth of MCV in Grafted Human Skin

Seventy-five immunocompromised mice received xenografts from fetal skins (25 mice), foreskins (37 mice) and adult skins (13 mice) and these xenografts were inoculated with MCV as described above. For the mice receiving fetal skins, 18 grafts were placed externally and 7 grafts were buried with epidermal side down. For the mice receiving foreskins, 6 grafts were placed externally, 9 grafts were buried with epidermal side up and 22 grafts were buried with epidermal side down. For the mice receiving adult skin, all 13 grafts were placed externally. The grafts were left undisturbed for at least 19 weeks before biopsies were taken. The growth of MCV in mice receiving these xenografts is described below. The data for all the 50 mice that received foreskins and adult skins is rendered in Table 1. The results of the data in all 75 mice, including the 25 mice that received fetal skin transplants, are summarized in Table 2.

1. Fetal Skin Xenografted Mice

Twenty-five immunocompromised mice were xenografted with skins from 14–24 week old fetuses according to the procedures described above. Of the 25 mice, 23 survived at least 19 weeks after inoculation of MCV. Human fetal skin was grafted externally and buried with epidermal side down. Although externally placed fetal grafts showed much less shrinkage than externally placed postnatal grafts, no growth of MCV occurred on or in any of the fetal skin grafts.

2. Foreskin Xenografted Mice

Thirty-seven immunocompromised mice were xenografted with human foreskins according to the procedures described above. Of these 37 mice, 27 survived at least 19 weeks. Of these 27 mice, MCV grew in 10 (37%) of the foreskin xenografts. The yield of growth in externally placed grafts was 17%. By contrast 43% of buried grafts grew MCV. The lower yield observed in external grafts was probably due to the shrinkage of such grafts.

3. Adult Skin Xenografted Mice

Thirteen immunocompromised mice were xenografted with adult skin pieces according to the procedures described above. Because of the thickness of most of these pieces, adult human skins obtained from surgical specimens were engrafted externally. Despite their initial thickness, significant shrinkage was observed. Of the 13 mice grafted, 8 survived at least 19 weeks, yet only 1 grew MCV, giving a yield of 13%.

4. Combined Postnatal Skin xenografted Mice

Of the 50 immunocompromised mice that received postnatal human skin grafts as described in Sections 2 and 3, 18 had xenografts sewn externally. Of these 18 mice, 2 grafts involuted to zero and 15 grafts involuted to >50% of the original surface area. Only one externally placed graft did not appreciably shrink in surface area, but no MCV grew on this graft. Of the 14 xenografts that endured at least 19 weeks, 2 grafts grew MCV, giving a 14% yield.

Of the same 50 mice, 9 had xenografts buried with epidermal surface facing up. One of the 9 died within one week of inoculation of MCV. Of the remaining 8, 5 mice lived at least 19 weeks and of these, 3 grew MCV, giving a 60% yield for this subgroup. Four of the 8 had grafts that externalized within 8 weeks of transplantation, and 3 of these 4 grafts involuted to zero. No MCV grew on these 3 grafts before their disappearance. The one remaining graft that externalized grew MCV. Of the 4 mice whose grafts either externalized after 8 weeks from the time of transplantation or did not externalize at all, 2 grew MCV.

Of the same 50 mice, 22 had xenografts (all foreskins) buried with epidermal surface facing down. Of these, 6 mice died prior to 19 weeks after inoculation of MCV and were lost to study. Of the remaining 16 mice, 7 were biopsied from 19 to 23 weeks after inoculation. These biopsies were done blindly, since the subcutaneous cysts that formed from the buried donor skin were not opened prior to biopsy. Four of the 7 showed growth of MCV on microscopic exam of the fixed tissue. Two of the 3 that were negative on biopsy subsequently were positive for MCV on autopsy, suggesting sampling error at the time of biopsy. Of the 16 mice that survived at least 19 weeks, 6 grew MCV, giving a 38% yield. Immunohistological analysis of infected human skin grafts from immunocompromised mice confirmed growth of MCV in these tissues.

h) Summary

Among mice that received postnatal xenografts and survived at least 19 weeks, growth of MCV occurred in 2 out of 14 mice (14%) whose xenografts were placed externally, in 3 of 5 mice (60%) whose xenografts were buried epidermal side up and in 6 of 16 (38%) mice whose xenografts were buried epidermal side down. However, among all mice that received postnatal xenografts, growth of MCV occurred in 2 out of 18 mice (11%) whose xenografts were placed externally, in 3 out of 9 mice (33%) whose xenografts were buried epidermal side up and in 6 of 22 ((27%) mice whose xenografts were buried epidermal side down. Growth of MCV occurred in xenografts examined 19 to 41 weeks after inoculation. Of the 50 immunocompromised mice, MCV grew on xenografts in 2 of 13 (15%) SCID mice, in 5 of 24 (21%) NOD SCID mice and in 4 of 11 (36%) N III nude mice.

TABLE 1

| Mouse I.D. No. | Skin type | Weeks Survived | MCV Expression | External Graft | Buried Graft (Epidermis Up) | Buried Graft (Epidermis down) |
|---|---|---|---|---|---|---|
| 1 | F | 3 | – | | X | |
| 2 | F | 1 | Not innoc. | | X | |
| 3 | F | 5 | – | | X | |
| 4 | F | 5 | – | | X | |
| 5 | A | 3 | – | X | | |
| 6 | F | 26 | – | X | | |
| 7 | A | 24 | – | X | | |
| 8 | A | 2 | – | X | | |
| 9 | A | 24 | – | X | | |
| 10 | F | 30 | – | X | | |
| 11 | F | 30 | – | X | | |
| 12 | F | 8 | – | | | X |
| 13 | F | 28 | – | X | | |
| 14 | F | 19 | + | X | | |
| 15 | A | 42 | – | X | | |
| 16 | A | 41 | + | X | | |
| 17 | A | 0 | – | X | | |
| 18 | A | 20 | – | X | | |
| 19 | A | 20 | – | X | | |
| 20 | F | 19 | – | | | X |
| 21 | F | 40 | + | | X | |
| 22 | F | 26 | – | X | | |
| 23 | F | 23 | – | | X | |
| 24 | F | 16 | – | | | X |
| 25 | F | 23 | – | | | X |
| 26 | F | 37 | + | | X | |
| 27 | Died | | – | | | |
| 28 | F | 35 | – | | X | |
| 29 | F | 35 | + | | X | |
| 30 | F | 34 | + | | | X |
| 31 | F | 14 | – | | | X |
| 32 | F | 21 | – | | | X |
| 33 | F | 21 | – | | | X |
| 34 | F | 13 | – | | | X |
| 35 | F | 20 | – | | | X |
| 36 | F | 37 | + | | | X |
| 37 | F | 23 | – | | | X |
| 38 | F | 22 | – | | | X |
| 39 | F | 31 | – | | | X |
| 40 | A | 21 | – | X | | |
| 41 | A | 10 | – | X | | |
| 42 | A | 21 | – | X | | |
| 43 | F | 29 | + | | X | |
| 44 | F | 25 | + | | X | |
| 45 | F | 33 | + | | X | |
| 46 | F | 9 | – | | X | |
| 47 | F | 1 | – | | X | |
| 48 | F | 28 | – | | X | |
| 49 | F | 24 | – | | X | |
| 50 | F | 32 | + | | X | |

Glossary
F = foreskin
A = adult skin

TABLE 2

| TYPE OF GRAFT | NUMBER OF MICE | NUMBER SURVIVING 19 WEEKS | NUMBER WITH MCV EXPRESSION |
|---|---|---|---|
| Fetal Tissue | 25 | 23 | 0 |
| External Graft | 18 | 17 | 0 |
| Buried Graft, Epidermal Side Up | 0 | | |

TABLE 2-continued

| TYPE OF GRAFT | NUMBER OF MICE | NUMBER SURVIVING 19 WEEKS | NUMBER WITH MCV EXPRESSION |
|---|---|---|---|
| Buried Graft, Epidermal Side Down | 7 | 6 | 0 |
| Foreskin Tissue | 37 | 27 | 10 |
| External Graft | 6 | 6 | 1 |
| Buried Graft, Epidermal Side Up | 9 | 5 | 3 |
| Buried Graft Epidermal Side Down | 22 | 16 | 6 |
| Adult Skin Tissue | 12 | 8 | 1 |
| External Graft | 12 | 8 | 1 |
| Buried Graft, Epidermal Side Up | 0 | | |
| Buried Graft, Epidermal Side Down | 0 | | |

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. A method for growing molluscum contaglosum virus (MCV) in human keratinocytes comprising:

preparing a xenograft of human epithelial tissue;

grafting the xenograft onto or into an immunocompromised host;

infecting the xenograft with MCV either before or after grafting the xenograft onto or into the immunocompromised host;

wherein the infection results in productive MCV replication and the production of progeny virus.

2. A system for expressing molluscum contaglosum virus (MCV) comprising:

a xenograft of human epithelial tissue infected with MCV grafted onto or into an immunocompromised host such that the infection results in productive MCV replication and the production of progeny virus.

3. The method according to claim 1 wherein the step of preparing a xenograft of human epithelial tissue includes exposing a sufficient area of a capillary bed surface of the immunocompromised host to support the xenograft; and the step of grafting the xenograft onto or into an immunocompromised host includes grafting the xenograft to the host such that a dermal side of the xenograft is in contact with the exposed area of the capillary bed surface.

4. The method according to claim 1 wherein the human epithelial tissue is postnatal skin.

5. The method according to claim 4 wherein the human epithelial tissue is a foreskin.

6. The method according to claim 1 wherein the human epithelial tissue is selected from the group consisting of glabrous skin, hair bearing skin and mucous membrane.

7. The method according to claim 1 wherein the host is an immunodeficient host.

8. The method according to claim 3, the step of exposing an area of a capillary bed surface including removing a section of skin from the immunocompromised host such that an area of a capillary bed surface on the immunocompromised host is exposed.

9. The method according to claim 3, the step of exposing an area of a capillary bed surface including uplifting a section of skin from a body of the immunocompromised host, and the step of grafting the xenograft including grafting the xenograft to the area of the capillary bed in a cutaneous site, a subcutaneous site within the body, or on the uplifted section of skin and grafting the uplifted skin section to the body of the host.

10. The method according to claim 8, wherein the step of uplifting the host skin section is performed such that the exposed capillary bed surface is positioned on the host body.

11. The method according to claim 10, wherein the step of grafting the xenograft includes grafting the xenograft to the host body.

12. The method according to claim 10, wherein the step of grafting the xenograft includes grafting the xenograft to the uplifted host skin section.

13. The method according to claim 9, wherein the step of uplifting the host skin section is performed such that the exposed capillary bed surface is positioned on the uplifted host skin section.

14. The method according to claim 13, wherein the step of grafting the xenograft includes grafting the xenograft to the host body.

15. The method according to claim 13, wherein the step of grafting the xenograft includes grafting the xenograft to the uplifted host skin section.

16. The expression system according to claim 2 wherein the xenograft of human epithelial tissue grafted onto or into an immunocompromised host is a xenograft in contact with an area of a capillary bed surface of the immunocompromised host.

17. The expression system according to claim 2 wherein the xenograft is postnatal skin or mucous membrane.

18. The expression system according to claim 2 wherein the immunocompromised host is a mammal whose immune system is genetically impaired.

19. The expression system according to claim 2 wherein the immunocompromised host is selected from the group consisting of SCID mice, NOD-SCID mice, nude mice, N-III nude mice and nude rats.

20. The expression system according to claim 16 wherein a host skin section is removed to expose a sufficient area of the capillary bed surface to support a tissue graft and the xenograft is attached to the area of the capillary bed surface at the location where the host skin section is removed.

21. The expression system according to claim 16 wherein a section of skin of the immunocompromised host is uplifted from a body of the immunocompromised host to expose a sufficient area of the capillary bed surface to support a tissue graft, the xenograft is grafted to either the body or the uplifted section of skin.

22. The method according to claim 7 wherein the immunodeficient host is selected from the group consisting of SCID mice, NOD-SCID mice, nude mice, N-III nude mice and nude rats.

23. The expression system according to claim 2 wherein complete replicative cycles of MCV occur for at least 2 weeks after infection.

* * * * *